United States Patent
Henry et al.

(10) Patent No.: US 11,706,559 B2
(45) Date of Patent: Jul. 18, 2023

(54) REPLACEABLE SOUND ATTENUATING DEVICE DETECTION

(71) Applicant: 3M INNOVATIVE PROPERTIES COMPANY, St. Paul, MN (US)

(72) Inventors: Paul D. Henry, Carmel, IN (US); Cameron J. Fackler, Indianapolis, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 337 days.

(21) Appl. No.: 15/733,072

(22) PCT Filed: Nov. 7, 2018

(86) PCT No.: PCT/IB2018/058740
§ 371 (c)(1),
(2) Date: May 7, 2020

(87) PCT Pub. No.: WO2019/092607
PCT Pub. Date: May 16, 2019

(65) Prior Publication Data
US 2020/0359125 A1 Nov. 12, 2020

Related U.S. Application Data

(60) Provisional application No. 62/582,803, filed on Nov. 7, 2017.

(51) Int. Cl.
*H04R 1/10* (2006.01)
*A61F 11/08* (2006.01)
(Continued)

(52) U.S. Cl.
CPC ............ *H04R 1/1083* (2013.01); *A61F 11/08* (2013.01); *G10K 11/16* (2013.01); *H04R 1/1008* (2013.01);
(Continued)

(58) Field of Classification Search
CPC .. H04R 1/1083; H04R 1/1008; H04R 1/1016; H04R 1/1041; H04R 2420/05;
(Continued)

(56) References Cited

U.S. PATENT DOCUMENTS

| 6,118,877 A | 9/2000 | Lindemann |
| 7,286,678 B1 * | 10/2007 | Bachler ................. H04R 25/70 |
| | | 381/314 |

(Continued)

FOREIGN PATENT DOCUMENTS

| CN | 105554616 | 5/2016 |
| CN | 106899908 | 6/2017 |

(Continued)

OTHER PUBLICATIONS

Extended EP Search Report, EP 18875258.8, dated Jul. 8, 2021, 7 pages.

(Continued)

*Primary Examiner* — Joseph Saunders, Jr.
(74) *Attorney, Agent, or Firm* — Katherine M. Scholz

(57) ABSTRACT

A sound attenuating apparatus may include a replaceable sound attenuating device and an electronic receiver configured to mate with the replaceable sound attenuating device. The replaceable sound attenuating device may include a sound attenuating material having an embedded sensor element. The sensor element may have a property that corresponds to a type of replaceable sound attenuating device. The electronic receiver may detect the property of the sensor element. A computing device may determine the type of the replaceable sound attenuating device from the property of the sensor element and perform one or more operations based on the type of replaceable sound attenuating device, including audio control, safety warnings, personal attenuation rating determinations, and the like.

14 Claims, 6 Drawing Sheets

(51) Int. Cl.
*G10K 11/16* (2006.01)
*A61F 11/14* (2006.01)

(52) U.S. Cl.
CPC ......... *H04R 1/1016* (2013.01); *H04R 1/1041* (2013.01); *A61F 11/145* (2022.01); *H04R 2420/05* (2013.01); *H04R 2420/07* (2013.01)

(58) Field of Classification Search
CPC .... H04R 2420/07; A61F 11/08; A61F 11/145; G10K 11/16
See application file for complete search history.

(56) References Cited

U.S. PATENT DOCUMENTS

| | | | |
|---|---|---|---|
| 8,340,338 B2 | 12/2012 | Mlodzikowski | |
| 8,774,434 B2 | 7/2014 | Zhao | |
| 9,172,345 B2 | 10/2015 | Kok | |
| 2006/0042866 A1 | 3/2006 | Widmer | |
| 2007/0009130 A1 | 1/2007 | Feeley | |
| 2007/0177749 A1 | 8/2007 | Sjusen | |
| 2008/0260193 A1 | 10/2008 | Westermann | |
| 2015/0139474 A1 | 5/2015 | Henry | |
| 2016/0286300 A1* | 9/2016 | Hussein | H04R 1/1016 |
| 2016/0360328 A1 | 12/2016 | Schmidt | |
| 2017/0041728 A1* | 2/2017 | Killion | H04R 25/652 |
| 2018/0192207 A1* | 7/2018 | Schmidt | H04R 25/60 |

FOREIGN PATENT DOCUMENTS

| | | |
|---|---|---|
| FR | 2845273 | 4/2004 |
| FR | 2849771 | 7/2004 |
| WO | WO 2015-001784 | 1/2015 |

OTHER PUBLICATIONS

Berger, "What is a Personal Attenuation Rating (PAR)?", 3M Occupational Health & Environmental Safety Division, Version 2.31, published on Apr. 2, 2010, 8 pages.

International Search Report for PCT International Application No. PCT/IB2018/058740, dated Feb. 12, 2019, 4 pages.

* cited by examiner

REPLACEABLE SOUND ATTENUATING DEVICE DETECTION

CROSS REFERENCE TO RELATED APPLICATIONS

This application is a national stage filing under 35 U.S.C. 371 of PCT/IB2018/058740, filed Nov. 7, 2018, which claims the benefit of U.S. Provisional Application No. 62/582,803, filed Nov. 7, 2017, the disclosure of which is incorporated by reference in its entirety herein.

TECHNICAL FIELD

The disclosure relates to personal protective equipment and, more specifically, to sound attenuating devices for hearing protection.

BACKGROUND

Sound attenuating devices are often used in, for example, industrial, military, and recreational applications. A sound attenuating device may protect a wearer from hearing damage by fitting to a wearer's head, such as in or around an ear, and reducing the effects of sound from the surrounding environment. A particular sound attenuating device may have various properties relating to, e.g., fit, manufacturer, intended receiver, and an associated sound attenuation rating that represents an average sound attenuation value and/or acoustic profile for various frequencies. Due to human anatomy, a particular sound attenuating device may fit differently on one wearer than another wearer, such that each wearer may experience a different level of sound attenuation.

SUMMARY

In accordance with techniques of this disclosure, a sound attenuating device may include a sensor element indicative of a type of the sound attenuating device. The type may be associated with sound attenuation properties of the sound attenuating device, such as a sound attenuation rating or acoustic profile for various frequencies. The sound attenuating device may be attached to a receiver that detects, based on the sensor element, the type of sound attenuating device attached. In some examples, the receiver may communicate with an external device to receive external information related to a user and/or an environment of the user.

The techniques may provide one or more advantages. For example, the receiver may use the detected type of the sound attenuating device, along with the external information, for a variety of operations such as indicating the suitability of the sound attenuating device for a particular environment or particular user, determining the fit of the sound attenuating device for the user, processing sound through the sound attenuating device, or communicating usage information of the sound attenuating device. As a result, the sound attenuating device may be more suitably matched for the particular work environment or user, may provide a more accurate fit determination for the particular user, may result in less distortion of the processed sound, or may provide useful usage information for the type of sound attenuating device than a sound attenuating device that does not utilize the type of sound attenuating device and the external information.

According to embodiments of the disclosure, a sound attenuating apparatus may include a replaceable sound attenuating device and an electronic receiver configured to mate with the replaceable sound attenuating device. The replaceable sound attenuating device may include a sound attenuating material having an embedded sensor element. The sensor element may have a property that corresponds to the type of replaceable sound attenuating device. The electronic receiver may detect the property of the sensor element. A computing device may determine the type of the replaceable sound attenuating device from the property of the sensor element and perform one or more operations based on the type of replaceable sound attenuating device, including audio control, safety warnings, personal attenuation rating determinations, and the like.

According to embodiments of the disclosure, a replaceable sound attenuating device includes a sound attenuating material and a sensor element embedded within the sound attenuating material. The sensor element has a property indicative of a type of the replaceable sound attenuating device.

According to embodiments of the disclosure, an electronic receiver for a replaceable sound attenuating device includes a body, transceiver, and processor circuitry. The body is configured to physically couple with the replaceable sound attenuating device. The replaceable sound attenuating device includes a sound attenuating material that includes a sensor embedded therein. The processor circuitry is coupled to the transceiver and configured to detect a coupling between the electronic receiver and the replaceable sound attenuating device and, responsive to the coupling, detect a property of the sensor element that corresponds to a type of the replaceable sound attenuating device.

According to embodiments of the disclosure, a sound attenuating apparatus includes a replaceable sound attenuating device and an electronic receiver for the replaceable sound attenuating device. The replaceable sound attenuating device includes a sound attenuating material having a sensor element embedded therein. The electronic receiver is configured to mate with the replaceable sound attenuating device and detect a property of the sensor element that corresponds to the type of the replaceable sound attenuating device.

According to embodiments of the disclosure, a hearing protection system includes a computing system for estimating an effectiveness of at least one replaceable sound attenuating device and an electronic receiver for the at least one replaceable sound attenuating device. The at least one replaceable sound attenuating device includes a sound attenuating material having a sensor element embedded therein. The electronic receiver is configured to mate with the at least one replaceable sound attenuating device, determine a type of the at least one replaceable sound attenuating device based at least on a property of the sensor element as detected by the electronic receiver, and transmit, to the computing system over a communication link, an indicator that represents the type of the at least one replaceable sound attenuating device. The computing system is configured to estimate the effectiveness of at least one replaceable sound attenuating device based at least on the indicator.

According to embodiments of the disclosure, a method includes, by an electronic receiver for a replaceable sound attenuating device comprising sound attenuating material having a sensor element embedded therein, detecting a coupling between the electronic receiver and the replaceable sound attenuating device, determining a type of the replaceable sound attenuating device based on a property of the sensor element and, responsive to a command, transmitting an indicator that represents the type of the replaceable sound attenuating device to a computing system over a communication link.

The details of one or more embodiments of the disclosure are set forth in the accompanying drawings and the description below. Other features, objects, and advantages of the disclosure will be apparent from the description and drawings, and from the claims.

BRIEF DESCRIPTION OF DRAWINGS

Like symbols in the drawings indicate like elements throughout the text and drawings.

DETAILED DESCRIPTION

Figure 1:
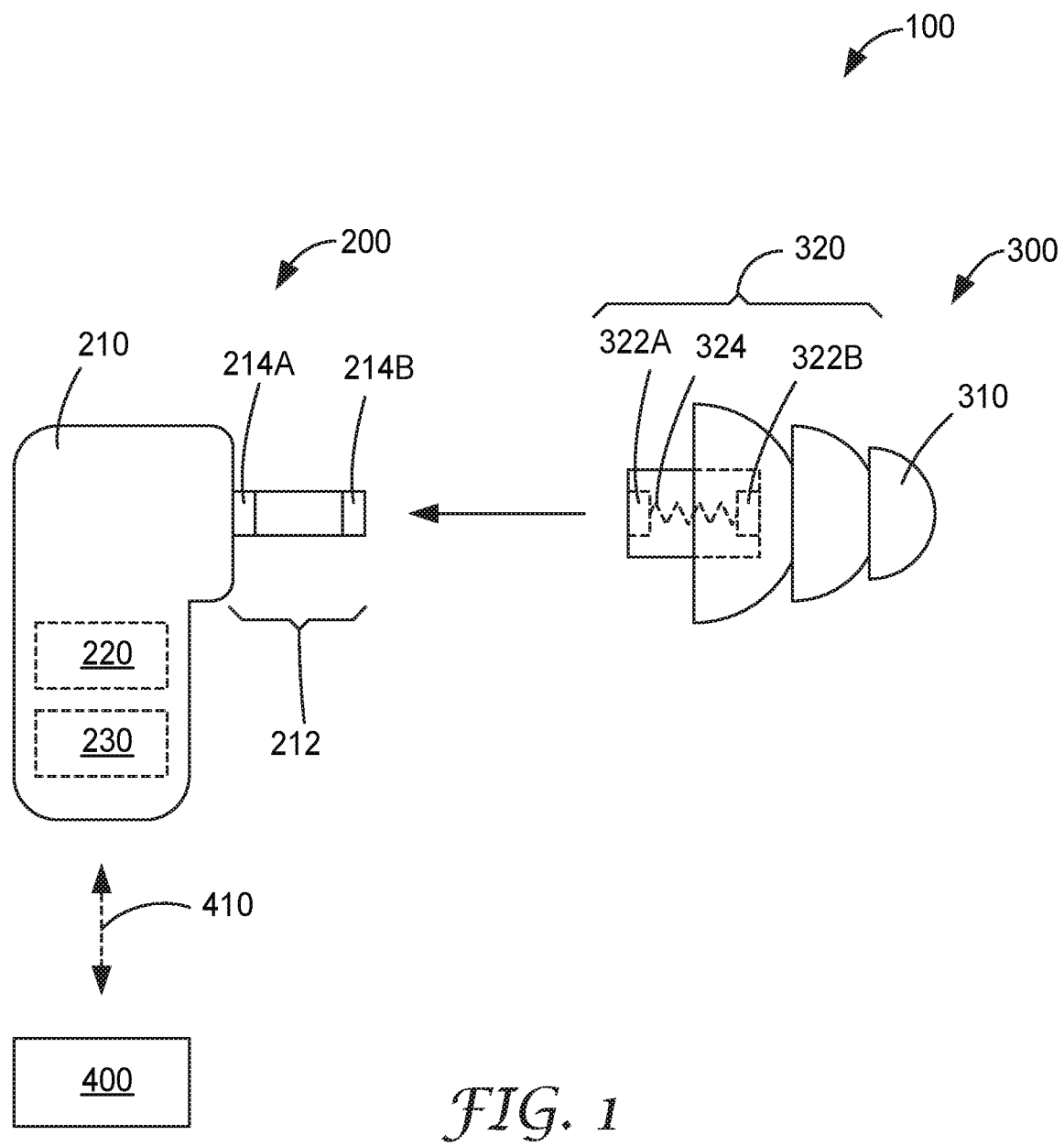
FIG. 1 is a side view of a sound attenuating apparatus as described herein.

FIG. 1 is a perspective view of a sound attenuating apparatus 100 according to techniques described herein. In some examples, sound attenuating apparatus 100 may be a hearing protection device to reduce an amount of airborne sound that directly enters the ear canal from that received from the surrounding environment. In some examples, sound attenuating apparatus 100 may be an electronic hearing protection device. In addition to being configured to reduce an amount of airborne sound from directly entering the ear canal, the electronic hearing protection device may include electronic components that are configured to receive airborne sound, convert the sound to electronic signals, process the electronic signals, convert the processed electronic signals into processed sound, and emit the processed sound through a speaker port.

Sound attenuating apparatus 100 may include an electronic receiver 200 and a replaceable sound attenuating device 300. Replaceable sound attenuating device 300 may be configured to interface with a user's ear and reduce an amount of airborne sound from directly entering the user's ear canal. For example, replaceable sound attenuating device 300 may include features designed to create a seal in or around a user's ear, such as an eartip or over-the-ear cushion.

Electronic receiver 200 may be configured to mate with replaceable sound attenuating device 300. Mating with replaceable sound attenuating device 300 may include any type of mechanism for physically coupling replaceable sound attenuating device 300 to electronic receiver 200 such that replaceable sound attenuating device 300 may not become detached from electronic receiver 200 during normal wear. Mating mechanisms may include, but are not limited to, friction, adhesion, ridges, and the like.

In some examples, electronic receiver 200 may include a body 210 configured to physically couple with replaceable sound attenuating device 300. In some examples, body 210 may include a receptacle 212 configured to physically couple with replaceable sound attenuating device 300. In some examples, receptacle 212 may include physical features that are configured to interface with one or more surfaces of replaceable sound attenuating device 300. For example, replaceable sound attenuating device 300 may include an inner cavity on a distal end that is configured to fit over receptacle 212, while receptacle 212 may include ridges that protrude outward into sides of the inner cavity of replaceable sound attenuating device 300. As another example, replaceable sound attenuating device 300 may be a cushion-type sound attenuating device that includes insets configured to receive clips of electronic receiver 200.

The fitting of at least a portion of sound attenuating device 300 into at least a portion of the ear canal or around the ear externally occludes the ear canal. In some examples, "externally occludes" means that at least some outward surfaces of sound attenuating device 300 are in sufficient contact with portions of the ear, such as the walls of the ear canal or the skin surrounding the ear (pinna), to reduce an amount of airborne sound from traveling into the ear canal in a space otherwise existing between sound attenuating device 300 and the ear canal walls or skin surrounding the ear so as to reach the inner ear.

Figure 4:
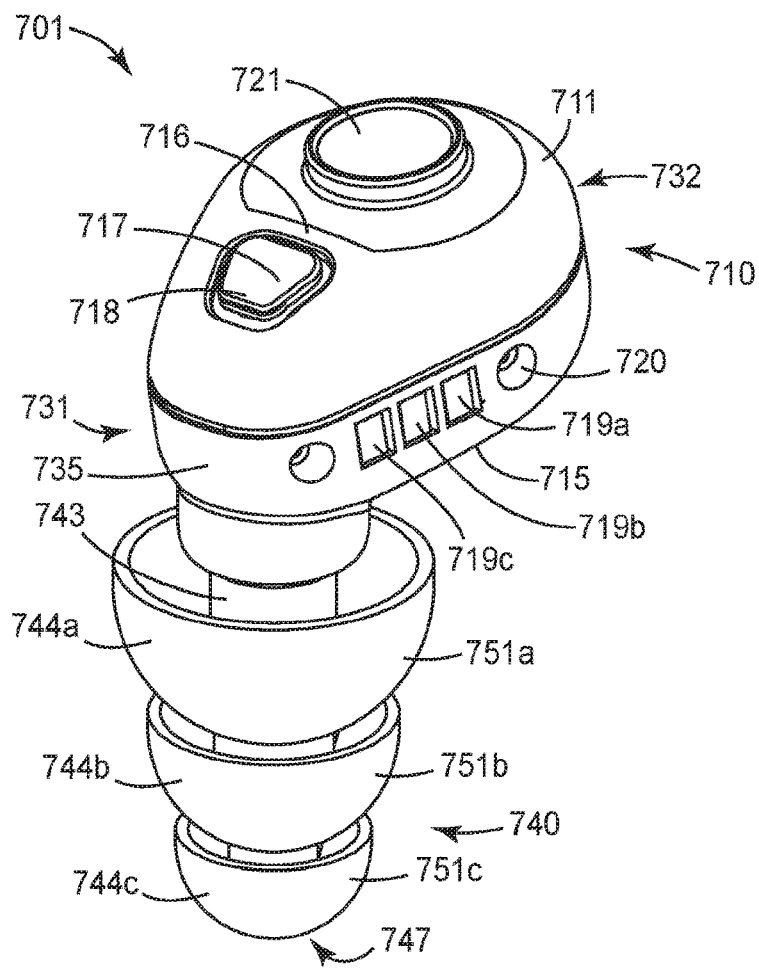
FIG. 4 is a perspective view of a sound attenuating apparatus as described herein.
Figure 5:
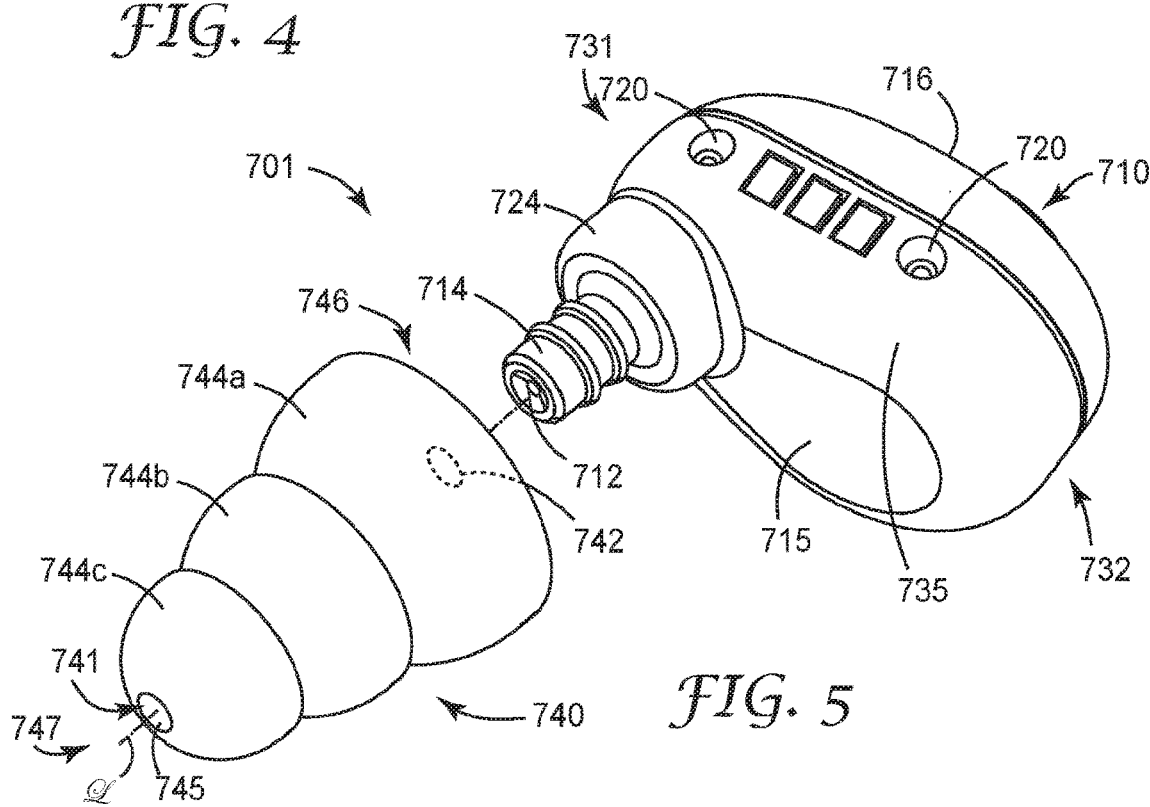
FIG. 5 is a perspective exploded view of a sound attenuating apparatus as described herein.

In some examples, electronic receiver 200 may perform electronic processing (e.g., so-called level-dependent processing that allows high intensity sounds to be electronically reduced while low intensity sounds can be passed through or even amplified), such that replaceable sound attenuating device 300 may include a through passage from a proximal end to a distal end to allow for passage of sound from a speaker of electronic receiver 200 to the ear canal of the user, as illustrated in the example of FIGS. 4 and 5. In this example, sound attenuating material alone may not completely occlude the ear canal, because a through passage may allow airborne sound to travel therethrough to reach the inner ear. Accordingly, the presence of electronic receiver 200 may serve to internally occlude replaceable sound attenuating device 300. By "internally occludes" is meant that electronic receiver 200 reduces an amount of airborne sound from entering a sound-receiving opening of replaceable sound attenuating device 300 while still allowing processed airborne sound to enter the opening. In this example, electronic receiver 200 may perform two separate functions, one electronic and one physical. The combination of the external occlusion of the ear canal achieved by replaceable sound attenuating device 300 and the internal occlusion of replaceable sound attenuating device 300 achieved by electronic receiver 200 can provide overall occlusion of the ear canal.

In some examples, replaceable sound attenuating device 300 may be configured as an eartip and electronic receiver 200 is configured as a concha-fit device and to interference-fit with the eartip. By eartip is meant a body of which at least major portions thereof are resiliently compressible and/or deformable at least in a radially inward direction, so that when the eartip is inserted into an ear canal, at least some portions of the eartip are resiliently biased radially outward so that at least some radially outward surfaces of the eartip are held against portions of the walls of the ear canal so as to substantially or completely eliminate any air gap therebetween. Such an eartip thus reduces an amount of airborne sound from traveling down the ear canal in a space between the eartip and the ear canal walls (the body of the eartip itself will of course reduce an amount of airborne sound from traveling through any space that the material of the eartip occupies). An example of an eartip may be shown in FIGS.

4 and 5 below. In some examples, replaceable sound attenuating device 300 is configured as a cushion and electronic receiver 200 is configured as an over-the-ear device and to adhere with the cushion.

Replaceable sound attenuating device 300 may include a sound attenuating material 310. Sound attenuating material 310 may be configured to reduce an amount of airborne sound from directly entering the user's ear canal. Properties of sound attenuating material 310 include, but are not limited to, shape, composition, size, compliance, conformability, compressibility, stiffness, damping, and the like. For example, for a replaceable sound attenuating device 300 that is an eartip, sound attenuating material 310 may include properties that exert an outward force to conform to an ear canal, while for a replaceable sound attenuating device 300 that is a cushion-type device, sound attenuating material 310 may include properties that, when combined with an external support such as a band, provide a spring force to hold replaceable sound attenuating device 300 against an outside of an ear. Sound attenuating material 310 may include any sound attenuating material capable of substantially attenuating sound to a desired level or by a desired amount including, but not limited to, polyurethanes, polyvinyl chlorides, thermoplastic elastomers, silicone, and the like.

Replaceable sound attenuating device 300 may have an associated type. The type of replaceable sound attenuating device 300 may be associated with a noise attenuation rating, such as a noise reduction rating (NRR), as well as other physical and acoustic features that affect passage of sound to and/or through replaceable sound attenuating device 300, such as dimensions of a through passage of an eartip-type replaceable sound attenuating device or cushion thickness of a cushion of a cushion-type replaceable sound attenuating device. The noise attenuation rating may be established through testing that accounts for all sound pathways to an ear, such as a real-ear attenuation at threshold (REAT) test. For example, in a REAT test, a user wearing replaceable sound attenuating device 300 may be subject to a ⅓ octave band of noise at seven or nine different frequencies ranging from 125 Hz to 8000 Hz. Due to the sensitivity of these noise attenuation tests, a laboratory environment is required to control for background noise and test signal distortion. The resulting noise attenuation rating may reflect an average of the results of the noise attenuation tests.

In some examples, the type of replaceable sound attenuating device 300 may be based at least in part on properties of sound attenuating material 310, including material and physical properties. Material properties may include compositional characteristics of sound attenuating material 310, such as density, porosity, damping, and the like. For example, a denser sound attenuating material 310 may provide a higher level of sound attenuation than a less dense material. Physical properties may include physical dimensions of replaceable sound attenuating device 300, such as outer diameter of replaceable sound attenuating device 300, inner diameter of sound channel, length of sound channel, length of stem, molding, cushion thickness, and the like. For example, fit types of replaceable sound attenuating device 300, such as expanding eartips, rigid flanged eartips, different lengths and diameters of sound channels, and different thicknesses of cushions, may have different sound attenuation effects, such as transmission of different frequencies to different extents or volume of air contained between an earmuff cup and a side of a user's head.

In accordance with techniques of this disclosure, replaceable sound attenuating device 300 includes a sensor element 320 embedded in or otherwise coupled to sound attenuating material 310. Sensor element 320 may be embedded in sound attenuating material 310 if sensor element 320 is physically coupled to or integrated in any way to sound attenuating material 310. Embedded may include adhered to, surrounded by, doped with, or any other means of coupling sensor element 320 to sound attenuating material 310.

Sensor element 320 may have a property capable of being sensed by electronic receiver 200. The property of sensor element 320 may be indicative of the type of replaceable sound attenuating device 300. The property of sensor element 320 may be any relatively stable property that is capable of being determined and differentiated for different types of replaceable sound attenuating device 300. A property may be relatively stable if it does not change more than, for example, 20% when replaceable sound attenuating device 300 is used during ordinary working conditions. For example, a passive component, such as a resistor, capacitor, or inductor, may be relatively stable if a respective property changes 5% or less.

Correspondingly, electronic receiver 200 may be configured to detect the property of sensor element 320. Electronic receiver 200 may include processor circuitry 220. Processor circuitry 220 may be configured to detect a coupling between electronic receiver 200 and replaceable sound attenuating device 300. For example, a first contact 214A and a second contact 214B on receptacle 212 may detect whether receptacle 212 is adequately coupled to replaceable sound attenuating device 300. In response to the detected coupling, processor circuitry 220 may be configured to detect the property of sensor element 320 that corresponds to the type of replaceable sound attenuating device 300.

Processor circuitry 220 may include components configured to interface with sensor element 320 and measure the property of sensor element 320. A component may measure the property of sensor element 320 if the component is capable of determining a value of the property that may be differentiated from values that are not associated with the type of replaceable sound attenuating device 300. For example, for properties that may be determined through a response to a stimulus, electronic receiver 200 may include components that send the stimulus, receive the response to the stimulus, and measure the response to the stimulus. As another example, for properties that may be determined through electrical contact, electronic receiver 200 may include components that create a physical connection for electrical communication and measure an electrical property through the electrical communication.

In some examples, sensor element 320 may be a circuit element and the property of sensor element 320 may be an electrical property of the circuit element. For example, the circuit element may be configured to complete a circuit and provide a measurable value that corresponds to the electrical property of the circuit element. Electronic receiver 200 may be configured with the circuit that includes components capable of measuring the electrical property of the circuit element. A wide variety of electrical properties may be used to indicate the type of replaceable sound attenuating device 300 including, but not limited to, resistance, capacitance, frequency, inductance, and the like. A wide variety of circuit elements may be used including, but not limited to, resistors, capacitors, inductors, and the like. The property of sensor element 320 may be a combination of such electrical properties, such as a resistance value and a capacitance value of the sensor element 320.

In some examples, the circuit element may be a two-terminal element that includes a first terminal 322A, a second terminal 322B, and a circuit component 324 having the measurable property. The two-terminal element may be configured to couple to circuitry of electronic receiver 200 that has a topology for the electrical property of the circuit element, such as an ohmic value or a frequency value. Electronic receiver 200 may include receptacle 212 that includes first contact 214A and second contact 214B configured to contact first terminal 322A and second terminal 322B, respectively.

In some examples, the property of the circuit element may correspond to an ohmic value of the circuit element such that the ohmic value may be indicative of the type of replaceable sound attenuating device 300. For example, the circuit element may include a resistor that has the ohmic value that is in a range of ohmic values associated with the type of replaceable sound attenuating device 300. The resistor may be a wire, a metal doped into a portion of sound attenuating material 310, or any other conductive element that has an associated resistance capable of being measured. In some examples, at least a portion of sound attenuating material 310 may include a conductive or semi-conductive dopant at a concentration and conductivity associated with a particular resistance. Electronic receiver 200 may include a topology for the ohmic value to be determined. For example, electronic receiver 200 may include a fixed current source configured to provide a current to the circuit element, a voltmeter configured to measure a voltage produced by the current, and a circuit to determine the ohmic value from the voltage.

In some examples, the property of the circuit element may correspond to a frequency value of the circuit element such that the frequency value may be indicative of the type of replaceable sound attenuating device 300. For example, the circuit element may include a resistor that, when present in an RLC circuit, creates a measurable harmonic frequency. As another example, the circuit element may be a piece of metal or magnetic material with a physical proximity to an oscillator in electronic receiver 200 that may affect a running frequency of the oscillator.

In some examples, sensor element 320 is a radio-frequency identification (RFID) device and the property of sensor element 320 may correspond to a bit value of the RFID device, such that the bit value may be indicative of the type of replaceable sound attenuating device 300 or a specific instance of the replaceable sound attenuating device 300. For example, replaceable sound attenuating device 300 may include a passive RFID tag embedded in sound attenuating material 310. Electronic receiver 200 may include an active RFID reader configured to emit radio energy to the RFID tag of replaceable sound attenuating device 300 and receive a signal from the RFID tag that corresponds to the bit value of the passive RFID tag.

Electronic receiver 200 may include transceiver 230. Transceiver 230 may be coupled to processor circuitry 220 and configured to transmit information from electronic receiver 200 to another system, such as a computing system 400 through a communication link 410. In some examples, transceiver 230 may be configured to transmit an indication of the property of sensor element 320, such as to computing system 400 through communication link 410.

In some examples, electronic receiver 200 may include additional components. In some examples, electronic receiver 200 may include sound processing components. For example, as illustrated in FIGS. 4 and 5 described below, electronic receiver 200 may include an external microphone configured to receive sound, circuitry configured to process the sound, and an internal speaker configured to emit the processed sound. In some examples, electronic receiver 200 may include components for testing attenuation of replaceable sound attenuating device 300. For example, as explained in FIG. 7 below, electronic receiver 200 may include an internal microphone configured to receive a test signal through replaceable sound attenuating device 300 and an external microphone configured to directly receive the test signal from outside replaceable sound attenuating device 300. In some examples, electronic receiver 200 may include an external speaker configured to create the test signal or emit an alarm.

Sound attenuating apparatus 100 may be part of a health monitoring system that includes a computing device configured to receive the indication of the property of sensor element 320 and determine the type of replaceable sound attenuating device 300 based on the property of sensor element 320. The computing device may be located at a variety of functional locations in the health monitoring system. For example, the computing device may be part of electronic receiver 200 so that a wearer has a local indication of the type of replaceable sound attenuating device. Alternatively, if electronic receiver 200 is desired to be small or simple, the computing device may be located at a remote location and accessed from electronic receiver 200 through a transceiver. As another example, a user may have an intermediate processing device, such as wearable communication hub 530 described in FIGS. 2 and 3, that includes the computing device and transceiver.

In some examples, computing system 400 may be configured to determine the type of replaceable sound attenuating device 300 based on a value of the property of sensor element 320 received from electronic receiver 200. Transceiver 230 of electronic receiver 200 may be configured to transmit an indicator of the property of sensor element 320 to computing system 400 over communication link 410. Computing system 400 may be configured to receive the property of sensor element 320 and determine the type of replaceable sound attenuating device 300 from the property of sensor element 320. Computing system 400 may be configured to perform an operation based on the type of replaceable sound attenuating device 300, as will be explained further below. For example, computing system 400 may include a look-up table that associates ranges of values of the property with different types of replaceable sound attenuating devices. Computing system 400 may receive the value of the property of sensor element 320, match the property value within a range of property values, and output an indicator of the type of replaceable sound attenuating device 300 that corresponds to the particular range of property values. Computing system 400 may be configured as, for example, a local computing device, such as a wearable communication hub or smartphone, or a remote computing system, such as a server, as described below in FIGS. 2 and 3.

In some examples, processor circuitry 220 of electronic receiver 200 may be configured to determine the type of replaceable sound attenuating device 300 based on the property of sensor element 320. Processor circuitry 220 may include, for example a look-up table that associates ranges of property values with different types of replaceable sound attenuating devices. Processor circuitry 220 may receive the value of the property of sensor element 320, match the value of the property of sensor element 320 with a range of property values, and output an indicator of the type of replaceable sound attenuating device 300 that corresponds to the particular range of values of the property. Transceiver 230 may be configured to transmit the indicator of the type of replaceable sound attenuating device 300, such as to computing system 400 through communication link 410. Processor circuitry 220 may be configured to control transceiver 230 to transmit, to computing system 400 through communication link 410, the indicator that represents the type of replaceable sound attenuating device 300.

Computing system 400 may be configured to determine or receive an indicator of the type of replaceable sound attenuating device 300 and use the type of replaceable sound attenuating device 300 as a basis for performing one or more operations. For example, the type of replaceable sound attenuating device 300 may be associated with a variety of properties of replaceable sound attenuating device 300, such as acoustic properties including a magnitude of sound attenuation, that may influence sound processing. As another example the type of replaceable sound attenuating device 300 may be used with other information, such as receiver information, location information, user information, or environmental information, to determine safety or behavior of a user of the replaceable sound attenuating device 300.

In some examples, a type of replaceable sound attenuating device 300 may be used to notify a user or other party of the type of replaceable sound attenuating device 300. For example, in some cases a user may be unable to determine the type of replaceable sound attenuating device 300 based on external features or packaging of the replaceable sound attenuating device 300. Processor circuitry 220 may be configured to notify a user of the type of replaceable sound attenuating device 300, such as visually through a user interface on electronic receiver 200 (e.g., an LCD screen indicating one or more digits) or any other type of output (e.g., audio, haptic, or other suitable output type).

In some examples, a type of replaceable sound attenuating device 300 may be used to notify a user or other party of the suitability of replaceable sound attenuating device 300 for a particular environment or location.

Electronic receiver 200 may include circuitry coupled to processor circuitry 220 and configured to acquire geo-location data for replaceable sound attenuating device 300. Geo-location data may include any data that indicates at least a location of replaceable sound attenuating device 300. Geo-location data may include, but is not limited to, GPS data, wi-fi location data, and the like. In some examples, the circuitry may include GPS receivers, wi-fi antennae and circuitry, and the like.

Processor circuitry 220 of electronic receiver 200 may be configured to receive an indicator of the type of replaceable sound attenuating device 300 and determine a noise attenuation rating, such as NRR or PAR based on the type of replaceable sound attenuating device. The noise attenuation rating may include any noise attenuation rating for any national, regional, industry, proprietary, or internal standard including, but not limited to noise reduction rating (NRR), Canada Class, Single Number Rating (SNR), Sound Level Conversion (SLC), personal attenuation rating (PAR) or the like. Processor circuitry 220 may be configured to receive the geo-location data that includes a location of replaceable sound attenuating device 300. Processor circuitry may be configured to control electronic receiver 200 to generate an audio cue representative of the location of replaceable sound attenuating device 300. For example, a location may be associated with a particular NRR or personal attenuation rating (PAR) required. Processor circuitry 220 may compare the location with a list of locations for which replaceable sound attenuating device 300 may be used and cause an audio output device of electronic receiver 200 to output an audio cue based on whether replaceable sound attenuating device may be used in the location.

In addition to location data, geo-location data may include additional information associated with location. The additional information may include safety information, such as anticipated noise levels of the location, actual noise levels of the location, or required noise attenuation rating for a replaceable sound attenuating device used in the location.

In some examples, processor circuitry 220 may be further configured to receive or determine a safety indicator of an anticipated noise level, an actual noise level, or a required or recommended noise attenuation rating for a replaceable sound attenuating device associated with the particular environment or location and determine a threshold safety level for the particular environment or location based on the safety indicator. For example, processor circuitry 220 may determine a particular attenuated noise level as the threshold safety level for a particular environment and an unattenuated noise level as the noise level that a replaceable sound attenuating device must be capable of reducing to less than or equal to the threshold safety level.

Processor circuitry 220 may be configured to determine whether the type of replaceable sound attenuating device 300 is capable or incapable of attenuating noise within the particular environment to meet the threshold safety level. For example, processor circuitry 220 may reduce the unattenuated noise level by the PAR to determine a projected noise level and determine whether the projected noise level exceeds the threshold safety level. Processor circuitry 220 may be further configured to control electronic receiver 200 to generate an audio cue to indicate effectiveness of replaceable sound attenuating device 300 within the particular environment. For example, processor circuitry may cause a speaker to indicate an audio signal associated with "capable" and another audio signal associated with "incapable".

In some examples, the type of replaceable sound attenuating device 300 may be used to determine a personal attenuation rating (PAR) for user with the type of replaceable sound attenuating device 300 or combination of type of replaceable sound attenuating device 300 and electronic receiver 200. As mentioned above, a comprehensive controlled audio test, such as a REAT test, may be used to determine a noise attenuation rating for the replaceable sound attenuating device 300. However, other tests may be used to determine fit that are less comprehensive but simpler or cheaper to perform. For example, a microphone in real ear (MIRE) test may be used to determine ear fit of the replaceable sound attenuating device 300. In a MIRE test, a microphone located outside the ear and a microphone located inside the ear and replaceable sound attenuating device 300 may receive an audio signal at each microphone. Differences between the audio signals may be evaluated to determine fit of a particular replaceable sound attenuating device 300.

The MIRE test may not be as comprehensive as the REAT test due to physiological differences between a real ear, used in a REAT test evaluation, and a microphone, used in a MIRE test evaluation. For example, a REAT test may account for an artifact known as physiological noise masking in which an occluded ear amplifies internal noises and masks the threshold, while a MIRE test, which uses a microphone, does not include the artifact. As another example, in a MIRE test, the internal microphone may be positioned at an end of an acoustic tube, such that properties of the acoustic tube may affect the received signal of the microphone. For more details on the MIRE test, see "What is a Personal Attenuation Rating?", E. H. Berger, 3M Occupational Health & Environmental Safety Division, Version 2.31 published Apr. 2, 2010, the contents of which are incorporated herein in its entirety.

However, differences between a controlled ear-based test, such as the REAT test, and a less controlled microphone-based test, such as the MIRE test, may be compensated for through the use of compensation factors. Compensation factors may be determined by comparing attenuation values for a REAT test with attenuation values for a MIRE test for a particular replaceable sound attenuating device and receiver. By knowing the type of replaceable sound attenuating device 300, compensation factors particular to the type of replaceable sound attenuating device 300, or combination of the type of replaceable sound attenuating device 300 and electronic receiver 200, may be applied for a more accurate measurement and fit of replaceable sound attenuating device 300. See, for example, FIG. 7 below.

In some examples, the type of replaceable sound attenuating device 300 may be used to adapt audio controls to more accurately or desirably process sound. As mentioned above, sound attenuating apparatus 100 may include electronic receiver 200 and replaceable sound attenuating device 300 configured to receive airborne sound, convert the sound to electronic signals, process the electronic signals, convert the processed electronic signals into processed sound, and emit the processed sound through a speaker port. Correspondingly, electronic receiver 200 may include an external microphone configured to receive sound, circuitry configured to process the sound, and an internal speaker configured to emit the processed sound.

In some examples, electronic receiver 200 may include circuitry coupled to processor circuitry 220 and configured to process audio signals attenuated by replaceable sound attenuating device 300 and received by electronic receiver 200. For example, the external speaker of electronic receiver 200 may receive audio and the circuitry may process the audio received from the external speaker to audio signals. The audio may be attenuated by replaceable sound attenuating device 300, such that a user may not receive the unprocessed audio or may receive the unprocessed audio at a volume that is too low.

In some examples, processor circuitry 220 may be configured to control electronic receiver 200 to output audio at a level that is a function of a level of the audio signals attenuated by replaceable sound attenuating device 300. The level of the audio signals may represent a volume of the audio signals. Processor circuitry 220 may be configured to modify a level of the audio signals, such as by filtering audio signals that exceed a volume threshold, muting audio signals that exceed a volume threshold, amplifying audio signals below a volume threshold, or the like. For example, processor circuitry 220 may include memory that stores an acoustic transfer function for replaceable sound attenuating device 300 previously characterized in a controlled environment. The transfer function may vary by type of replaceable sound attenuating device 300 and may be configured to improve fidelity of transmitted sound based on the type of replaceable sound attenuating device 300 for electronic receiver 200. For example, the transfer function may be in a form of a one third octave band by band compensating adjustment. Processor circuitry 220 may control an internal speaker of electronic receiver 200 to output audio at the modified level based on, for example, the transfer function.

In some examples, processor circuitry 220 may be configured to control electronic receiver 200 to output audio based on audio characteristics of the type of replaceable sound attenuating device 300. The type of replaceable sound attenuating device 300 may be associated with various properties that affect the acoustics of sound emitted from an internal speaker located at an end of electronic receiver 200. For example, the properties of sound attenuating material 310, shape of sound attenuating material 310, length of through passage of replaceable sound attenuating device 300, and other surfaces and components that may contact sound emitted from the internal speaker, may affect the quality and characteristics of sound received by the wearer.

In some examples, the type of replaceable sound attenuating device 300 may be used with usage data to, for example, develop usage statistics for the type of replaceable sound attenuating device 300. Usage date may include, for example, usage location, usage environment, time of wear of replaceable sound attenuating device 300, usage with other equipment such as hoods or breathing apparatuses, and the like. Electronic receiver 200 may include circuitry that is coupled to processor circuitry 220 and configured to acquire usage data for replaceable sound attenuating device 300. Processor circuitry 220 may be configured to control transceiver 230 to transmit the usage data for replaceable sound attenuating device 300 to, for example, computing system 400 over communication link 410.

Figure 2:
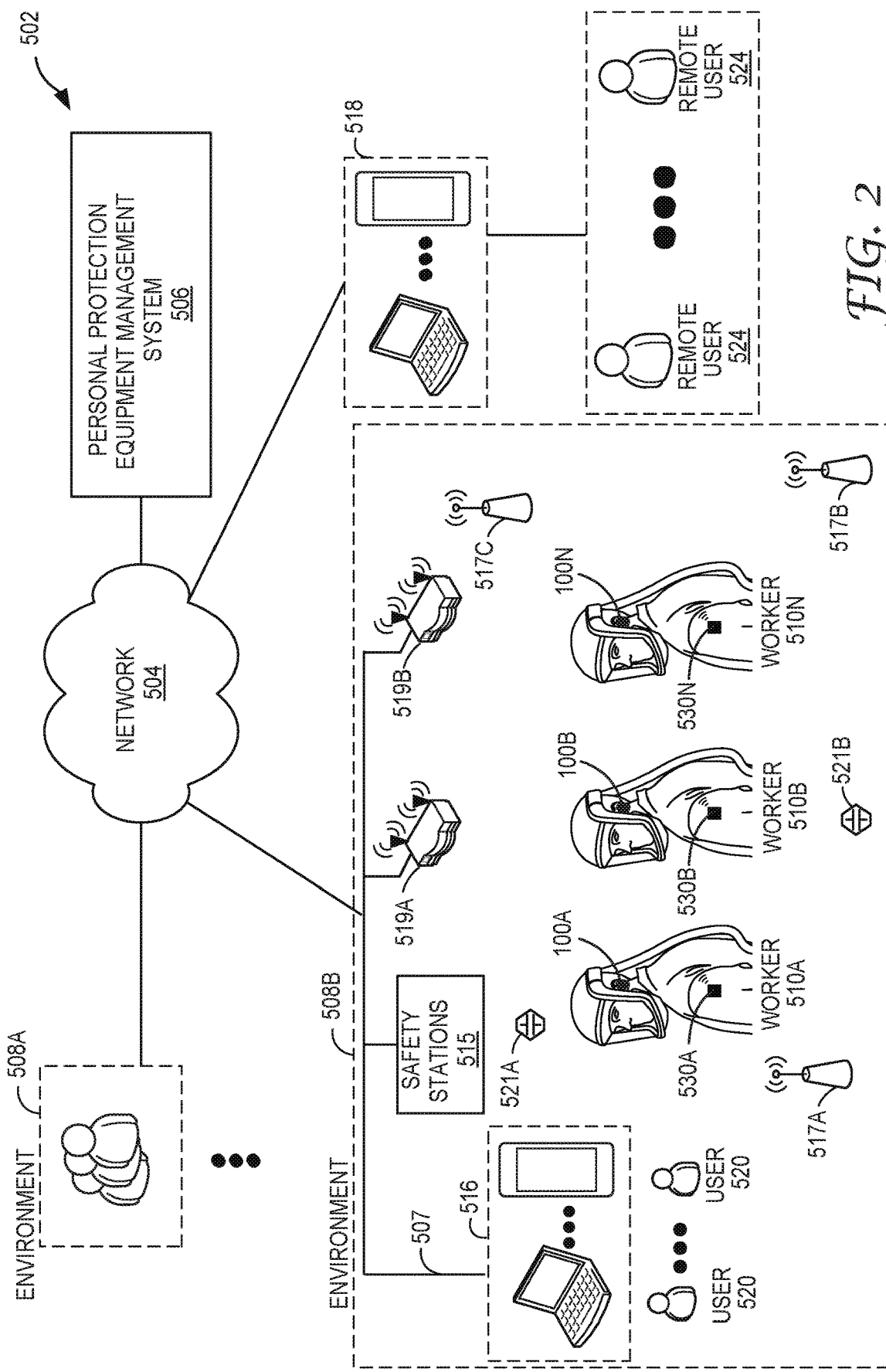
FIG. 2 is a block diagram illustrating an example hearing protection system as described herein.

FIG. 2 is a block diagram illustrating an example hearing protection system 502 that includes a personal protection equipment management system (PPEMS) 506 for managing personal protection equipment. As described herein, PPEMS allows authorized users to perform preventive occupational health and safety actions and manage inspections and maintenance of safety protective equipment. By interacting with PPEMS 506, safety professionals can, for example, manage area inspections, worker inspections, worker health and safety compliance training.

In general, PPEMS 506 provides data acquisition, monitoring, activity logging, reporting, predictive analytics, and alert generation. For example, PPEMS 506 includes an underlying analytics and safety event prediction engine and alerting system in accordance with various examples described herein. In general, a safety event may refer to activities of a user of personal protective equipment (PPE), a condition of the PPE, or a hazardous environmental condition. For example, in the context of hearing protection equipment, a safety event may be misuse of the hearing protection equipment, a user of the hearing protection equipment experiencing a high level of sound, an increase in a level of sound above an anticipated level of sound for which the hearing protection equipment is designed, or a failure of the hearing protection equipment.

As further described below, PPEMS 506 provides an integrated suite of personal safety protection equipment management tools and implements various techniques of this disclosure. That is, PPEMS 506 provides an integrated, end-to-end system for managing personal protection equipment, e.g., safety equipment, used by workers 8 within one or more physical environments 508, which may be construction sites, mining or manufacturing sites or any physical environment. The techniques of this disclosure may be realized within various parts of hearing protection system 502.

As shown in the example of FIG. 2, hearing protection system 502 represents a computing environment in which a computing device within of a plurality of physical environments 508A, 508B (collectively, environments 508) electronically communicate with PPEMS 506 via one or more computer networks 504. Each of physical environment 508 represents a physical environment, such as a work environment, in which one or more individuals, such as workers 510, utilize personal protection equipment while engaging in tasks or activities within the respective environment.

In this example, environment 508A is shown as generally having workers 510, while environment 508B is shown in expanded form to provide a more detailed example. In the example of FIG. 1, a plurality of workers 510A-510N are shown as utilizing respective sound attenuating apparatuses 100A-100N.

As further described herein, each of sound attenuating apparatuses 100 includes embedded sensors or monitoring devices and processing electronics configured to capture data in real-time as a user (e.g., worker) engages in activities while wearing the sound attenuating devices. For example, as described in FIG. 1, sound attenuating apparatuses 100 may include a number of sensors for sensing or controlling the operation and/or characteristics of such components. A sensor may include, for example, sensor element 320 of replaceable sound attenuating device 300 for indicating a type of replaceable sound attenuating device 300. Each sensor may generate usage data, as described herein.

In addition, each of sound attenuating apparatuses 100 may include one or more output devices for outputting data that is indicative of operation and/or characteristics of sound attenuating apparatuses 100 and/or generating and outputting communications to the respective worker 510. For example, sound attenuating apparatuses 100 may include one or more devices to generate audible feedback (e.g., one or more speakers), visual feedback (e.g., one or more displays, light emitting diodes (LEDs) or the like), tactile feedback (e.g., a device that vibrates or provides other haptic feedback), or wired/wireless communications.

In general, each of environments 508 include computing facilities (e.g., a local area network) by which sound attenuating apparatuses 100 are able to communicate with PPEMS 506. For examples, environments 508 may be configured with wireless technology, such as 802.11 wireless networks, 802.15 ZigBee networks, and the like. In the example of FIG. 2, environment 508B includes a local network 507 that provides a packet-based transport medium for communicating with PPEMS 506 via network 504. In addition, environment 508B includes a plurality of wireless access points 519A, 519B that may be geographically distributed throughout the environment to provide support for wireless communications throughout the work environment.

Each of sound attenuating apparatuses 100 may be configured to communicate data, such as sensed sounds, events, and conditions, via wireless communications, such as via 802.11 Wi-Fi protocols, Bluetooth protocol or the like. Sound attenuating apparatuses 100 may, for example, communicate directly with a wireless access point 519. As another example, each worker 510 may be equipped with a respective one of wearable communication hubs 530A-530M that enable and facilitate communication between sound attenuating apparatuses 100 and PPEMS 506. For example, sound attenuating apparatus 100, as well as other PPEs (such as fall protection equipment, respirators, hardhats, or other equipment) for the corresponding worker 510 may communicate with a corresponding communication hub 530 work by the worker 510 via Bluetooth or other short-range protocol, and the communication hubs 530 may communicate with PPEMs 506 via wireless communications processed by wireless access points 519. Although shown as wearable devices, hubs 530 may be implemented as stand-alone devices deployed within environment 508B. In some examples, hubs 530 may be articles of PPE.

In general, each of hubs 530 operates as a wireless device for sound attenuating apparatuses 100 relaying communications to and from sound attenuating apparatuses 100, and may be capable of buffering usage data in case communication is lost with PPEMS 506. Moreover, each of hubs 530 is programmable via PPEMS 506 so that local alert rules may be installed and executed without requiring a connection to the cloud. As such, each of hubs 530 provides a relay of streams of usage data from sound attenuating apparatuses 100 and/or other PPEs within the respective environment, and provides a local computing environment for localized alerting based on streams of events in the event communication with PPEMS 506 is lost.

As shown in the example of FIG. 2, an environment, such as environment 508B, may also include one or more wireless-enabled beacons, such as beacons 517A-517C, that provide accurate location information within the work environment. For example, beacons 517A-517C may be GPS-enabled such that a controller within the respective beacon may be able to precisely determine the position of the respective beacon. Based on wireless communications with one or more of beacons 517, a given sound attenuating apparatuses 100 or communication hub 530 worn by a worker 510 may be configured to determine the location of the worker within work environment 508B. In this way, event data reported to PPEMS 506 may be stamped with positional information to aid analysis, reporting and analytics performed by PPEMS 506.

In addition, an environment, such as environment 508B, may also include one or more wireless-enabled sensing stations, such as sensing stations 521A, 521B. Each sensing station 521 includes one or more sensors and a controller configured to output data indicative of sensed environmental conditions. Moreover, sensing stations 521 may be positioned within respective geographic regions of environment 508B or otherwise interact with beacons 517 to determine respective positions and include such positional information when reporting environmental data to PPEMS 506. As such, PPEMS 506 may be configured to correlate the sensed environmental conditions with the particular regions and, therefore, may utilize the captured environmental data when processing event data received from sound attenuating apparatuses 100. For example, PPEMS 506 may utilize the environmental data to aid generating alerts or other instructions for sound attenuating apparatuses 100 and for performing predictive analytics, such as determining any correlations between certain environmental conditions (e.g., heat, humidity, visibility) with abnormal worker behavior or increased safety events. As such, PPEMS 506 may utilize current environmental conditions to aid prediction and avoidance of imminent safety events. Example environmental conditions that may be sensed by sensing stations 521 include but are not limited to sensing noise, temperature, humidity, presence of gas, pressure, visibility, wind, and the like.

In example implementations, an environment, such as environment 508B, may also include one or more safety stations 515 distributed throughout the environment to provide viewing stations for accessing sound attenuating apparatuses 100. Safety stations 515 may allow one of workers 510 to check out sound attenuating apparatuses 100 and/or other safety equipment, verify that safety equipment is appropriate for a particular one of environments 508, and/or exchange data. For example, safety stations 515 may transmit alert rules, software updates, or firmware updates to sound attenuating apparatuses 100 or other equipment. Safety stations 515 may also receive data cached on sound attenuating apparatuses 100, hubs 530, and/or other safety equipment. That is, while sound attenuating apparatuses 100

(and/or communication hubs 530) may typically transmit usage data from sensors of sound attenuating apparatuses 100 to network 504 in real time or near real time, in some instances, sound attenuating apparatuses 100 (and/or communication hubs 530) may not have connectivity to network 504. In such instances, sound attenuating apparatuses 100 (and/or communication hubs 530) may store usage data locally and transmit the usage data to safety stations 515 upon being in proximity with safety stations 515. Safety stations 515 may then upload the data from sound attenuating apparatuses 100 (and/or communication hubs 530) and connect to network 504. In some examples, safety stations 515 may be configured to administer a fit test to a user. For example, safety stations 515 may include a speaker that emits an external signal, such as the external signal described in FIG. 7, to a user.

In addition, each of environments 508 include computing facilities that provide an operating environment for end-user computing devices 516 for interacting with PPEMS 506 via network 504. For example, each of environments 508 typically includes one or more safety managers responsible for overseeing safety compliance within the environment. In general, each user 520 interacts with computing devices 516 to access PPEMS 506. Each of environments 508 may include systems. Similarly, remote users 524 may use computing devices 518 to interact with PPEMS 506 via network 504. For purposes of example, the end-user computing devices 516 may be laptops, desktop computers, mobile devices such as tablets or so-called smart phones and the like.

Users 520, 524 interact with PPEMS 506 to control and actively manage many aspects of safely equipment utilized by workers 510, such as accessing and viewing usage records, analytics, and reporting. For example, users 520, 524 may review usage information acquired and stored by PPEMS 506, where the usage information may include data specifying starting and ending times over a time duration (e.g., a day, a week, or the like), data collected during particular events, such as incidences of sound above a particular volume from sound attenuating apparatuses 100, removal of sound attenuating apparatuses 100 from a head of workers 10, changes to operating parameters of sound attenuating apparatuses 100, status changes to components of sound attenuating apparatuses 100 (e.g., a low battery event), motion of workers 510, detected impacts to sound attenuating apparatuses 100 or hubs 530, sensed data acquired from the user, environment data, and the like. In addition, users 520, 524 may interact with PPEMS 506 to perform asset tracking and to schedule maintenance events for individual pieces of safety equipment, e.g., sound attenuating apparatuses 100, to ensure compliance with any procedures or regulations. PPEMS 506 may allow users 520, 524 to create and complete digital checklists with respect to the maintenance procedures and to synchronize any results of the procedures from computing devices 516, 518 to PPEMS 506.

Further, as described herein, PPEMS 506 integrates an event processing platform configured to process concurrent streams of events from digitally enabled PPEs, such as sound attenuating apparatuses 100. An underlying analytics engine of PPEMS 506 applies historical data and models to the inbound streams to compute assertions, such as identified anomalies or predicted occurrences of safety events based on conditions or behavior patterns of workers 510. Further, PPEMS 506 provides real-time alerting and reporting to notify workers 510 and/or users 520, 524 of any predicted events, anomalies, trends, and the like.

The analytics engine of PPEMS 506 may, in some examples, apply analytics to identify relationships or correlations between sensed worker data, environmental conditions, geographic regions and other factors and analyze the impact on safety events. PPEMS 506 may determine, based on the data acquired across populations of workers 510, which particular activities, possibly within certain geographic region, lead to, or are predicted to lead to, unusually high occurrences of safety events.

In this way, PPEMS 506 tightly integrates comprehensive tools for managing personal protection equipment with an underlying analytics engine and communication system to provide data acquisition, monitoring, activity logging, reporting, behavior analytics and alert generation. Moreover, PPEMS 506 provides a communication system for operation and utilization by and between the various elements of hearing protection system 502. Users 520, 524 may access PPEMS to view results on any analytics performed by PPEMS 506 on data acquired from workers 510. In some examples, PPEMS 506 may present a web-based interface via a web server (e.g., an HTTP server) or client-side applications may be deployed for devices of computing devices 516, 518 used by users 520, 524, such as desktop computers, laptop computers, mobile devices such as smartphones and tablets, or the like.

In some examples, PPEMS 506 may provide a database query engine for directly querying PPEMS 506 to view acquired safety information, compliance information and any results of the analytic engine, e.g., by the way of dashboards, alert notifications, reports, and the like. That is, users 524, 526, or software executing on computing devices 516, 518, may submit queries to PPEMS 506 and receive data corresponding to the queries for presentation in the form of one or more reports or dashboards. Such dashboards may provide various insights regarding hearing protection system 502, such as baseline ("normal") operation across worker populations, identifications of any anomalous workers engaging in abnormal activities that may potentially expose the worker to risks, identifications of any geographic regions within environments 508 for which unusually anomalous (e.g., high) safety events have been or are predicted to occur, identifications of any of environments 508 exhibiting anomalous occurrences of safety events relative to other environments, and the like.

As illustrated in detail below, PPEMS 506 may simplify workflows for individuals charged with monitoring and ensure safety compliance for an entity or environment. That is, the techniques of this disclosure may enable active safety management and allow an organization to take preventative or correction actions with respect to certain regions within environments 508, particular pieces of safety equipment or individual workers 510, define and may further allow the entity to implement workflow procedures that are data-driven by an underlying analytical engine.

As one example, the underlying analytical engine of PPEMS 506 may be configured to compute and present customer-defined metrics for worker populations within a given environment 508 or across multiple environments for an organization as a whole. For example, PPEMS 506 may be configured to acquire data and provide aggregated performance metrics and predicted behavior analytics across a worker population (e.g., across workers 510 of either or both of environments 508A, 508B). Furthermore, users 520, 524 may set benchmarks for occurrence of any safety incidences, and PPEMS 506 may track actual performance metrics relative to the benchmarks for individuals or defined worker populations.

As another example, PPEMS 506 may further trigger an alert if certain combinations of conditions are present, e.g., to accelerate examination or service of a safety equipment, such as one of sound attenuating apparatuses 100. In this manner, PPEMS 506 may identify individual sound attenuating apparatuses 100 or workers 510 for which the metrics do not meet the benchmarks and prompt the users to intervene and/or perform procedures to improve the metrics relative to the benchmarks, thereby ensuring compliance and actively managing safety for workers 510.

Figure 3:
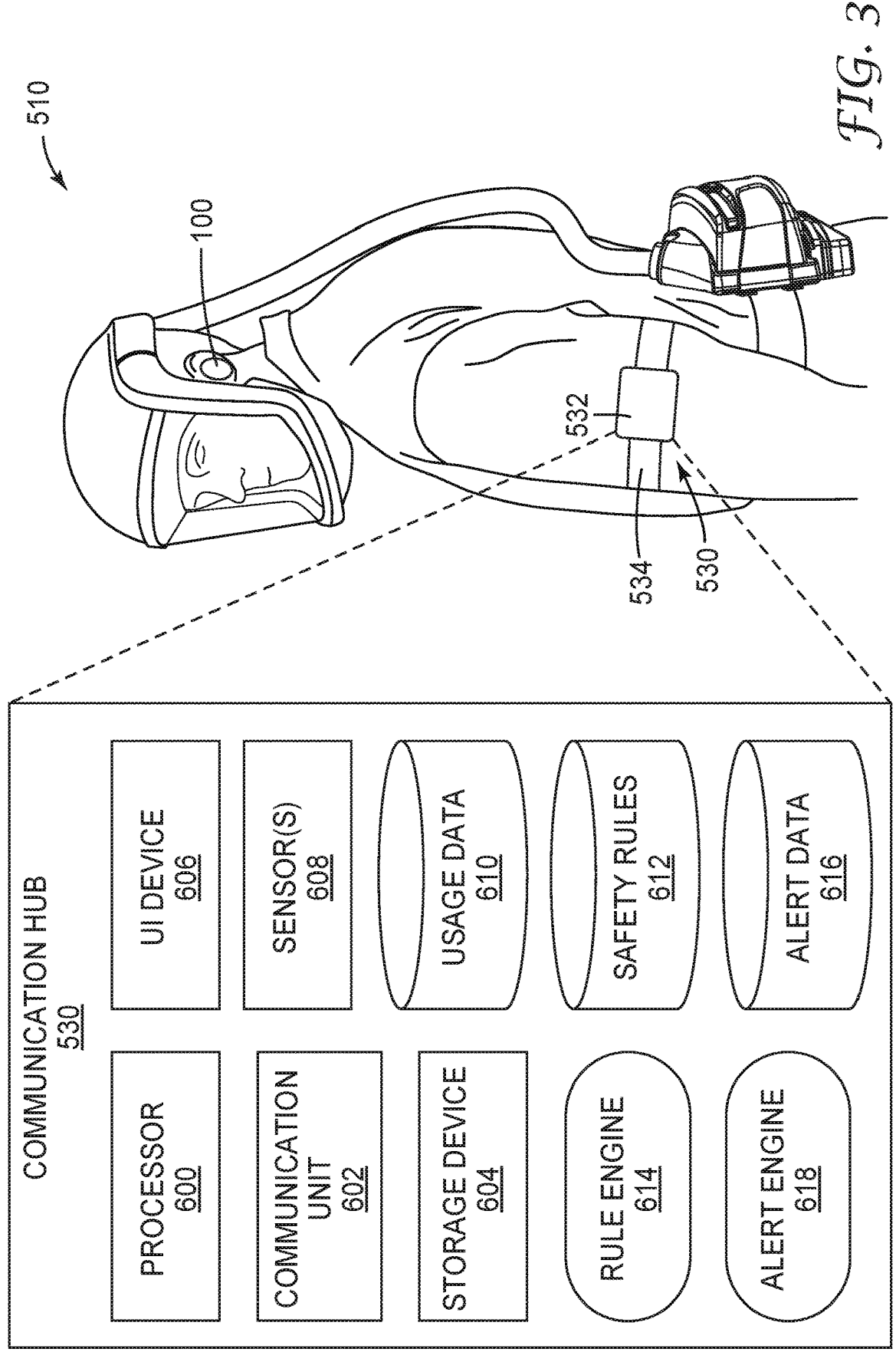
FIG. 3 is a conceptual diagram illustrating an example of a sound attenuating apparatus in communication with a communication hub as described herein.

FIG. 3 is a conceptual diagram illustrating an example of a sound attenuating apparatus in communication with a communication hub as described herein. FIG. 3 illustrates components of communication hub 530 including processor 600, communication unit 602, storage device 604, user-interface (UI) device 606, sensors 608, usage data 610, safety rules 612, rule engine 614, alert data 616, and alert engine 618. As noted above, communication hub 530 represents one example of hubs 530 shown in FIG. 2. FIG. 3 illustrates only one particular example of communication hub 530, as shown in FIG. 3. Many other examples of communication hub 530 may be used in other instances and may include a subset of the components included in example communication hub 530 or may include additional components not shown example communication hub 530 in FIG. 3.

In some examples, communication hub 530 may be an intrinsically safe computing device, smartphone, wrist- or head-worn computing device, or any other computing device that may include a set, subset, or superset of functionality or components as shown in communication hub 530. Communication channels may interconnect each of the components in communication hub 530 for inter-component communications (physically, communicatively, and/or operatively). In some examples, communication channels may include a hardware bus, a network connection, one or more inter-process communication data structures, or any other components for communicating data between hardware and/or software.

Communication hub 530 may also include a power source, such as a battery, to provide power to components shown in communication hub 530. A rechargeable battery, such as a Lithium Ion battery, can provide a compact and long-life source of power. Communication hub 530 may be adapted to have electrical contacts exposed or accessible from the exterior of the hub to allow recharging the communication hub 530. As noted above, communication hub 530 may be portable such that it can be carried or worn by a user. Communication hub 530 can also be personal, such that it is used by an individual and communicates with personal protective equipment (PPE) assigned to that individual. In FIG. 3, communication hub 530 is secured to a user using a strap 534. However, communication hub may be carried by a user or secured to a user in other ways, such as being secured to PPE being worn by the user, to other garments being worn to a user, being attached to a belt, band, buckle, clip, or other attachment mechanism as will be apparent to one of skill in the art upon reading the present disclosure.

One or more processors 600 may implement functionality and/or execute instructions within communication hub 530. For example, processor 600 may receive and execute instructions stored by storage device 604. These instructions executed by processor 600 may cause communication hub 530 to store and/or modify information, within storage devices 604 during program execution. Processors 600 may execute instructions of components, such as rule engine 614 and alert engine 618 to perform one or more operations in accordance with techniques of this disclosure. That is, rule engine 614 and alert engine 618 may be operable by processor 600 to perform various functions described herein.

In some examples, at least one of processors 600 may be configured as computing system 400 described in FIG. 1. For example, at least one of processors 600 may be configured to receive an indicator of a type of replaceable sound attenuating device 300 from electronic receiver 200 and perform an operation based on the type of replaceable sound attenuating device 300. As another example, at least one of processors 600 may be configured to receive a value of a property of sensor element 320 from electronic receiver 200, determine the type of replaceable sound attenuating device 300 based on the value of the property of sensor element 320, and perform an operation based on the type of replaceable sound attenuating device 300.

One or more communication units 602 of communication hub 530 may communicate with external devices by transmitting and/or receiving data. For example, communication hub 530 may use communication units 602 to transmit and/or receive radio signals on a radio network such as a cellular radio network. In some examples, communication units 602 may transmit and/or receive satellite signals on a satellite network such as a Global Positioning System (GPS) network. Examples of communication units 602 include a network interface card (e.g. such as an Ethernet card), an optical transceiver, a radio-frequency transceiver, a GPS receiver, or any other type of device that can send and/or receive information. Other examples of communication units 602 may include Bluetooth®, GPS, 3G, 4G, and Wi-Fi® radios found in mobile devices as well as Universal Serial Bus (USB) controllers and the like.

One or more storage devices 604 within communication hub 530 may store information for processing during operation of communication hub 530. In some examples, storage device 604 is a temporary memory, meaning that a primary purpose of storage device 604 is not long-term storage. Storage device 604 may be configured for short-term storage of information as volatile memory and therefore not retain stored contents if deactivated. Examples of volatile memories include random access memories (RAM), dynamic random-access memories (DRAM), static random-access memories (SRAM), and other forms of volatile memories known in the art.

Storage device 604 may, in some examples, also include one or more computer-readable storage media. Storage device 604 may be configured to store larger amounts of information than volatile memory. Storage device 604 may further be configured for long-term storage of information as non-volatile memory space and retain information after activate/off cycles. Examples of non-volatile memories include magnetic hard discs, optical discs, floppy discs, flash memories, or forms of electrically programmable memories (EPROM) or electrically erasable and programmable (EEPROM) memories. Storage device 604 may store program instructions and/or data associated with components such as rule engine 614 and alert engine 618.

UI device 606 may be configured to receive user input and/or output information to a user. One or more input components of UI device 606 may receive input. Examples of input are tactile, audio, kinetic, and optical input, to name only a few examples. UI device 606 of communication hub 530, in one example, include a mouse, keyboard, voice responsive system, video camera, buttons, control pad, microphone or any other type of device for detecting input from a human or machine. In some examples, UI device 606 may be a presence-sensitive input component, which may include a presence-sensitive screen, touch-sensitive screen, etc.

One or more output components of UI device 606 may generate output. Examples of output are data, tactile, audio, and video output. Output components of UI device 606, in some examples, include a presence-sensitive screen, sound card, video graphics adapter card, speaker, cathode ray tube (CRT) monitor, liquid crystal display (LCD), or any other type of device for generating output to a human or machine. Output components may include display components such as cathode ray tube (CRT) monitor, liquid crystal display (LCD), Light-Emitting Diode (LED) or any other type of device for generating tactile, audio, and/or visual output. Output components may be integrated with communication hub 530 in some examples.

UI device 606 may include a display, lights, buttons, keys (such as arrow or other indicator keys), and may be able to provide alerts to the user in a variety of ways, such as by sounding an alarm or vibrating. The user interface can be used for a variety of functions. For example, a user may be able to acknowledge or snooze an alert through the user interface. The user interface may also be used to control settings for sound attenuating apparatus 100 or other peripherals that are not immediately within the reach of the user. For example, sound attenuating apparatus 100 may be worn under a respirator such that the wearer cannot access the controls without removing the respirator.

Sensors 608 may include one or more sensors that generate data indicative of an activity of a worker 510 associated with hub 530 and/or data indicative of an environment in which hub 530 is located. Sensors 608 may include, as examples, one or more accelerometers, one or more sensors to detect conditions present in a particular environment (e.g., sensors for measuring temperature, humidity, particulate content, noise levels, air quality, or any variety of other characteristics of environments in which sound attenuating apparatuses 100 may be used), or a variety of other sensors.

Communication hub 530 may store usage data 610 from components of sound attenuating apparatus 100. For example, as described herein, components of sound attenuating apparatus 100 may generate data regarding operation of sound attenuating apparatus 100 that is indicative of activities of worker 510 and transmit the data in real-time or near real-time to hub 530. Usage data may include, for example, the noise level data.

In some examples, hub 530 may immediately relay usage data 610 to another computing device, such as PPEMS 506, via communication unit 602. In other examples, storage device 604 may store usage data 610 for some time prior to uploading the data to another device. For example, in some instances, communication unit 602 may be able to communicate with sound attenuating apparatus 100 but may not have network connectivity, e.g., due to an environment in which sound attenuating apparatus 100 is located and/or network outages. In such instances, hub 530 may store usage data 610 to storage device 604, which may allow usage data 610 to be uploaded to another device upon a network connection becoming available.

Communication hub 530 may store safety rules 612 as described in this disclosure. Safety rules 612 may be stored in any suitable data store as described in this disclosure. As examples for purposes of illustration, safety rules 612 may include threshold information both for a length of time a worker 510 is allowed to be exposed to a particular noise level before an alert is generated, and the level or type of replaceable sound attenuating device 300 of sound attenuating apparatus 100 that will trigger an alert. For example, when communication hub 530 receives information from an environmental beacon that there are no noise hazards present in the environment, the threshold of time for the worker 510 being in the particular location may be infinite. If a hazard is present in the environment, then the threshold may be determined based upon the concern of the threat to the user. For example, high noise levels may require assignment of the threshold to be on the order of minutes or hours.

Communication hub 530 may store data related to types of replaceable sound attenuating devices. Data related to types of replaceable sound attenuating devices may include any information that may be associated with a type of replaceable sound attenuating device, including values of a property of a sensor element in a replaceable sound attenuating device that correspond to the type of the replaceable sound attenuating device. For example, communication hub may receive a value of a property for sensor element 320 and look up the value of the property in a look-up table that includes ranges of values of the property associated with types of replaceable sound attenuating devices. Communication hub 530 may also store user data associated with the type of replaceable sound attenuating device. For example, communication hub 530 may access a personal attenuation rating (PAR) based on a previous test for a worker 510 for the type of replaceable sound attenuating device 300.

Thresholds for a noise level can be used to predict, e.g., by PPEMS 506, hearing loss and lower levels of noise exposure and/or frequent breaks can be recommended to the user. Thresholds can be used for predicted battery run time. As the battery nears selectable remaining run time, the user can be notified/warned to complete their current task and seek a fresh battery. When a threshold is exceeded for a specific environmental hazard, an urgent alert can be given to the user to evacuate the immediate area. Thresholds can be customized to various noise levels of sound attenuating apparatus 100. In other words, a threshold for the amount of exposure to a noise level without triggering an alarm may be longer if the noise level is low as compared to if a noise level is higher, or may be longer if the type of replaceable sound attenuating device 300 provides higher levels of sound attenuation compared to a type of replaceable sound attenuating device 300 that provides less sound attenuation.

Reaching different thresholds set forth in safety rules 612 may result in triggering different types of alerts or alarms. For example, alarms may be informational (not requiring a user response), urgent (repeated and requiring a response or acknowledgement from a user), or emergency (requiring immediate action from a user.) The type of alert or alarm can be tailored to the environment. Different types of alerts and alarms can be coupled together to get user attention. In some instances, a user may be able to "snooze" an alert or alarm.

Rule engine 614 may be a combination of hardware and software that executes one or more safety rules, such as safety rules 612. For instance, rule engine 614 may determine which safety rules to execute based on context data, information included in the safety rule set, other information received from PPEMS 506 or other computing devices, user input from the worker, or any other source of data that indicates which safety rules to execute. In some examples, safety rules 612 may be installed prior to a worker entering a work environment, while in other examples, safety rules 612 be dynamically retrieved by communication hub 530 based on context data generated at first particular point in time.

Rule engine 614 may execute safety rules periodically, continuously, or asynchronously. For instance, rule engine 614 may execute safety rules periodically by evaluating the conditions of such rules each time a particular time interval passes or expires (e.g., every second, every minute, etc.). In some examples, rule engine 614 may execute safety rules continuously by checking such conditions using one or more scheduling techniques that continuously evaluate the conditions of such rules. In some examples, rule engine 614 may execute safety rules asynchronously, such as in response to detecting an event. An event may be any detectable occurrence, such as moving to a new location, detecting a worker, coming within a threshold distance of another object, or any other detectable occurrence.

Rule engine 614, upon determining that a condition of a safety rule has or has not been satisfied may perform one or more actions associated with the safety rule by executing one or more operations that define the actions. For instance, rule engine 614 may execute a condition that determines (a) if a worker is approaching or has entered a work environment, (b) whether sound attenuating apparatus 100 is being worn by the worker and (c) whether replaceable sound attenuating device 300 of sound attenuating apparatus 100 is of a particular type of replaceable sound attenuating device that is adequate for the environment, e.g., a type of replaceable sound attenuating device that is rated for a particular noise level. This safety rule may specify actions if the condition is not satisfied which cause rule engine 614 to generate an alert at communication hub 530 using UI device 606 and send a message using communication unit 602 to PPEMS 506, which may cause PPEMS 506 to send a notification to a remote user (e.g., the safety manager).

Alert data 616 may be used for generating alerts for output by UI device 606. For example, hub 530 may receive alert data from PPEMS 506, end-user computing devices 516, remote users using computing devices 518, safety stations 515, or other computing devices. In some examples, alert data 616 may be based on operation of sound attenuating apparatus 100. For example, hub 530 may receive alert data 616 that indicates a status of sound attenuating apparatus 100, that sound attenuating apparatus 100 is appropriate for the environment in which sound attenuating apparatus 100 is located, that the environment in which sound attenuating apparatus 100 is located is unsafe, or the like.

In some examples, additionally or alternatively, hub 530 may receive alert data 616 associated with a likelihood of a safety event. For example, as noted above, PPEMS 506 may, in some examples, apply historical data and models to usage data from sound attenuating apparatus 100 in order to compute assertions, such as anomalies or predicted occurrences of imminent safety events based on environmental conditions or behavior patterns of a worker 510 using sound attenuating apparatus 100. That is, PPEMS 506 may apply analytics to identify relationships or correlations between sensed data from sound attenuating apparatus 100, environmental conditions of an environment in which sound attenuating apparatus 100 is located, a geographic region in which sound attenuating apparatus 100 is located, and/or other factors. PPEMS 506 may determine, based on the data acquired across populations of workers 510, which particular activities, possibly within certain environment or geographic region, lead to, or are predicted to lead to, unusually high occurrences of safety events. Hub 530 may receive alert data 616 from PPEMS 506 that indicates a relatively high likelihood of a safety event.

Alert engine 618 may be a combination of hardware and software that interprets alert data 616 and generate an output at UI device 606 (e.g., an audible, visual, or tactile output) to notify worker 510 of the alert condition (e.g., that the likelihood of a safety event is relatively high, that the environment is dangerous, that sound attenuating apparatus 100 is malfunctioning, that one or more components of sound attenuating apparatus 100 need to be repaired or replaced, or the like). In some instances, alert engine 618 may also interpret alert data 616 and issue one or more commands to sound attenuating apparatus 100 to modify operation or enforce rules of sound attenuating apparatus 100 in order to bring operation of sound attenuating apparatus 100 into compliance with desired/less risky behavior. For example, alert engine 618 may issue commands that control the operation of electronic receiver 200.

FIG. 4 is a perspective view of a sound attenuating apparatus 701, while FIG. 5 is a perspective exploded view of the sound attenuating apparatus 701 of FIG. 4, as described herein. As shown in FIGS. 4 and 5, sound attenuating apparatus 701 includes two major components eartip 740 and earpiece body 710. Eartip 740 and earpiece body 710 may include the features of replaceable sound attenuating device 300 and electronic receiver 200, respectively, of FIG. 1. Eartip 740 is configured (i.e., is shaped and sized and is comprised of a material of suitable softness) to fit into the ear canal of the user's ear. Earpiece body 710 is configured (i.e., shaped and sized) to fit into the concha of a human user's ear and is configured to receive sound, to perform appropriate signal processing, and to emit processed sound through a speaker port.

Eartip 740 is detachably attached to earpiece body 710 so that eartip 740 can be removed and cleaned or replaced if desired. Eartip 740 includes a through-passage 741 that extends through eartip 740 and allows the passage of airborne sound therethrough. Through-passage 741 includes a first, sound-receiving opening 742 that is acoustically mated to a speaker port 712 of earpiece body 710, and a second, sound emitting opening 745 that faces toward the inner ear of the user, so that processed sound that is emitted from the speaker port can be transmitted through internal through-passage 741 and directed therefrom toward the inner ear of the user.

Eartip 740 includes a long axis L that, when sound attenuating apparatus 701 is fitted in the ear of a human user, will typically be at least generally aligned with a long axis of the portion of the ear canal into which the eartip is fitted. Eartip 740 includes an outward end 746 and an inward end 747, outward end 746 being the end that is attached to earpiece body 710 and inward end 747 being the end that resides closest to the inner ear of the user. In the example of FIGS. 4 and 5, eartip 740 may include a main body 743 that includes one or more radially-outward-protruding flanges 744 made of a resiliently deformable material. Insertion of such an eartip into an ear canal may result in such flanges being deformed, with the desired resilient biasing of surfaces 751 of the flanges against the walls of the ear canal being thus achieved.

Earpiece body 710 includes a housing 711 which may be comprised of e.g. a molded polymeric material. Housing 711 may be configured so that sound attenuating apparatus 701 may be held in position in a human ear by way of at least one contact surface of housing 711 of earpiece body 710 of sound attenuating apparatus 701 being adjacent to (e.g., in contact with) a skin surface that defines at least a portion of the radially outer perimeter of a user's concha, in combination with the fitting of eartip 740 into a user's ear canal. Housing 711 of earpiece body 710 may be provided in a generally oval shape having an end 731, opposite end 732, sidewall surface 735, outward surface 716, and inward surface 715. In the example of FIGS. 4 and 5, housing 711 is of generally oval shape with end 731 being somewhat narrower than opposite end 732.

Earpiece body 710 may include an internal battery, a microphone 717 for receiving airborne sound and converting the received sound to electronic signals, a windscreen 718 for protecting microphone 717, circuitry for processing the electronic signals, a speaker for transducing the processed signals into airborne processed sound, one or more electrical connections (three such connections 719*a*, 719*b*, and 719*c* are shown in FIGS. 4 and 5) by which an internal battery of sound attenuating apparatus 701 can be recharged, and/or to allow communication with an external appliance (e.g. for configuring or programming sound attenuating apparatus 701), one or more physical alignment features (e.g., sockets or protrusions) 720 to aid in aligning earpiece body 710 with a recharging unit and/or an external appliance, one or more switches 721 (of any suitable type, e.g. a touch-sensitive switch) to perform any desired function (e.g., turning the device on and off, switching between settings, increasing or decreasing volume, attenuation/gain, or any other parameter, and so on), and the like.

Speaker port 712 of earpiece body 710 may be conveniently provided in a location which allows a first, sound-receiving opening 742 of through-passage 741 of eartip 740 to be acoustically mated thereto. In the example of FIGS. 4 and 5, speaker port 712 may be provided at the terminal end of a protrusion 714 from a speaker housing 724 that extends inward so that when outward end 746 of eartip 740 is attached to protrusion 714, speaker port 712 and opening 742 of eartip 740 are aligned with each other and are in close proximity to each other. Eartip 740 may be attached to earpiece body 710 (e.g., outward end 746 of eartip is attached to protrusion 714 of earpiece body 710) in a detachable manner. In the example of FIGS. 4 and 5, detachable attachment of eartip 740 to earpiece body 710 may be provided by a friction fit of an annular portion of main body 743 of eartip onto the radially outer surface of protrusion (post) 714. As illustrated in FIGS. 4 and 5, one or more ridges or barbs may be provided on post 714 to enhance the friction fit and yet to allow the eartip to be manually removed when desired.

While FIGS. 4 and 5 describe a sound attenuating apparatus as including a concha-fit device and an eartip, in other examples, the sound attenuating apparatus may include an over-the-ear device and a cushion. In some examples, electronic receiver 200 may be an over-the-ear device, such as an earmuff, that is configured with electronic components and features as described in FIGS. 4 and 5. For example, the over-the-ear device may include an internal battery, a microphone, a windscreen for protecting the microphone, circuitry for processing the electronic signals, a speaker for transducing the processed signals into airborne processed sound, one or more electrical connections by which the internal battery can be recharged and/or to allow communication with an external appliance, one or more physical alignment to aid in aligning an earpiece body with a recharging unit and/or an external appliance, one or more switches to perform any desired function, a speaker port, and the like. In some examples, replaceable sound attenuating device 300 may be a cushion, such as a circular outer cushion of an earmuff, configured to adhere to the over-the-ear device and substantially form a seal against a head of a user around an ear of the user. For example, the cushion may be detachably attached to the over-the-ear device so that the cushion can be removed and cleaned or replaced if desired and may be configured to receive sound, perform appropriate signal processing, and emit processed sound through a speaker port.

Figure 6:
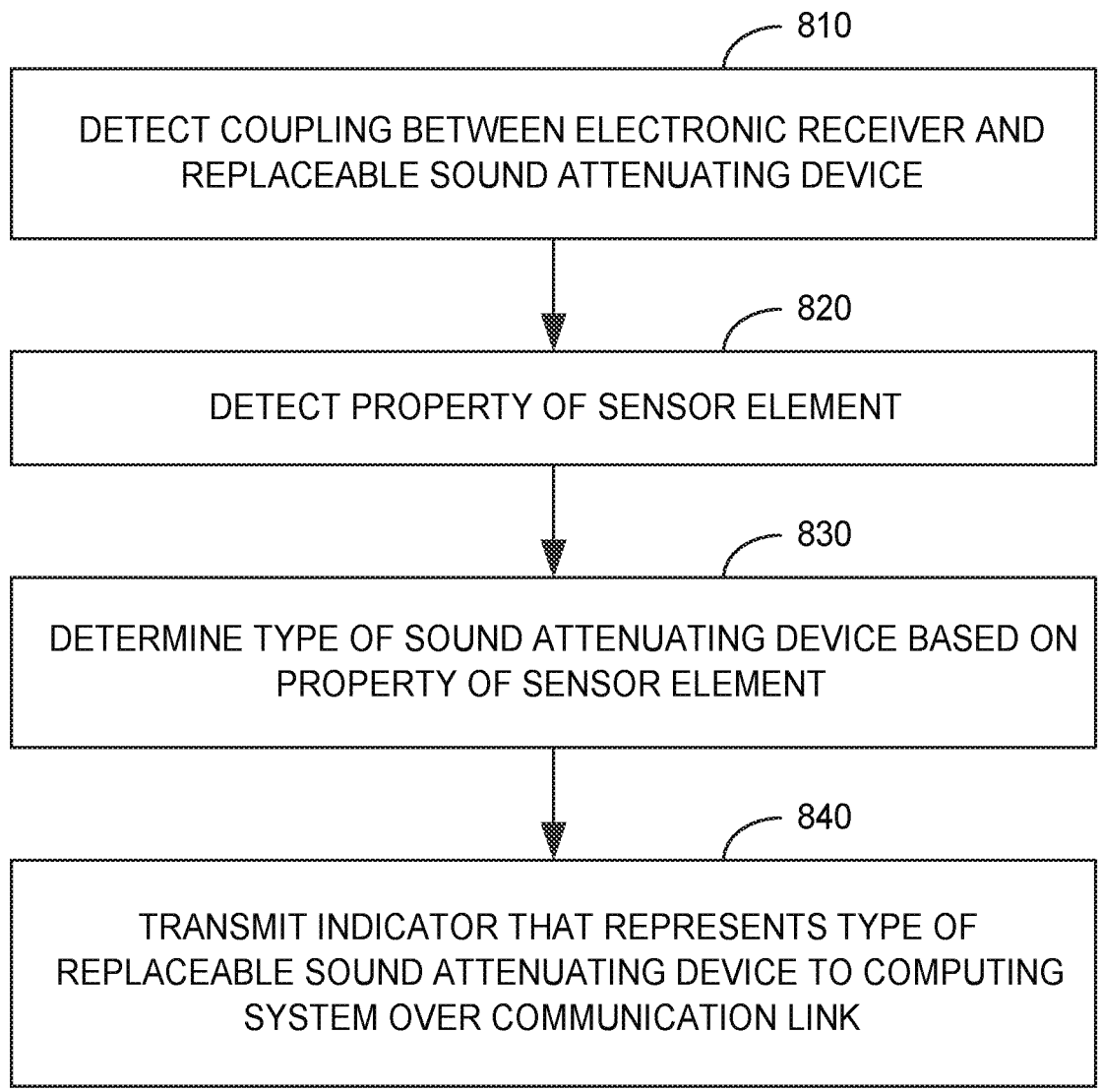
FIG. 6 is a flowchart of a method of using a sound attenuating apparatus as described herein.

FIG. 6 is a flowchart of a method of determining an indicator of a type of replaceable sound attenuating device 300 as described herein. Electronic receiver 200 may detect a coupling between electronic receiver 200 and replaceable sound attenuating device 300 (810). In some examples, electronic receiver 200 may detect a coupling between electronic receiver 200 and replaceable sound attenuating device 300 by sending a stimulus to replaceable sound attenuating device 300 and receiving an anticipated response caused by the stimulus from replaceable sound attenuating device 300 that is indicative of coupling between electronic receiver 200 and replaceable sound attenuating device 300. For example, in examples where sensor element 320 is a circuit element, electronic receiver 200 may create a potential difference between contacts 214A and 214B (stimulus) and detect whether current flows between contacts 214A and 214B (response), indicating a closed circuit formed by contacts 214A and 214B and the circuit element (coupling).

Electronic receiver 200 may detect a property of sensor element 320 (820). In some examples, electronic receiver 200 may detect the property by measuring the property of sensor element 320. For example, in examples where sensor element 320 is a resistor, electronic receiver 200 may create a potential difference between contacts 214A and 214B, measure current flow, and determine a resistance from the potential difference and the current flow. As another example, in examples where sensor element 320 is an RFID tag, electronic receiver 200 may emit radio energy to the RFID tag of replaceable sound attenuating device 300 and receive a signal from the RFID tag that corresponds to the bit value of the passive RFID tag. Electronic receiver 200 may measure the bit value of the passive RFID tag.

Electronic receiver 200 may determine a type of replaceable sound attenuating device 300 based on the property of sensor element 320 (830). In some examples, electronic receiver 200 may determine the type of replaceable sound attenuating device 300 by associating a measurement of the property with a reference. For example, electronic receiver 200 may match the value of the property of sensor element 320 with a range of property values and output an indicator of the type of replaceable sound attenuating device 300 that corresponds to the particular range of values of the property.

Electronic receiver 200 may transmit an indicator that represents the type of replaceable sound attenuating device 300 to computing system 400 (840). In some examples, electronic receiver 200 transmits a measured value for the property of sensor element 320 to computing system 400 in lieu of determining the type of replaceable sound attenuating device 300 and transmitting the indicator thereof.

Figure 7:
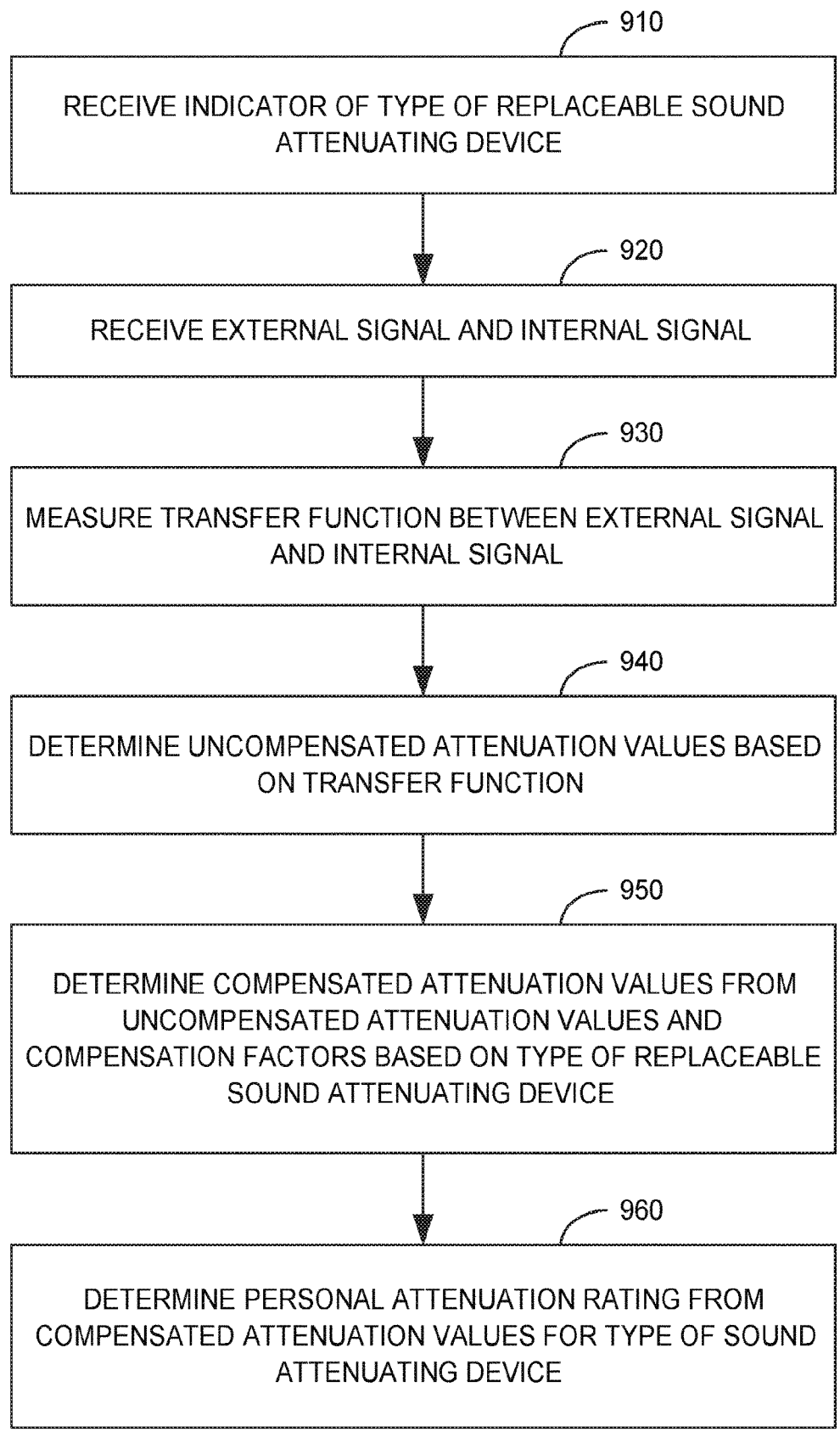
FIG. 7 is a flowchart of a method for estimating an effectiveness of a replaceable sound attenuating device as described herein.

FIG. 7 is a flowchart of a method for estimating an effectiveness of replaceable sound attenuating device 300 based at least on the indicator of the type of replaceable sound attenuating device 300 of sound attenuating apparatus 100. A user may wear replaceable sound attenuating device 300. In some examples, replaceable sound attenuating device 300 may be coupled to electronic receiver 200 that includes an internal microphone and an external microphone, while in other examples, a testing device may include an internal microphone that may be positioned in replaceable sound attenuating device 300 and an external microphone that may be positioned outside replaceable sound attenuating device 300. Computing system 400 may be communicatively coupled through communication link 410 to the internal microphone and the external microphone, such as by transceiver 230 for electronic receiver 200 or a cable for the testing device discussed above.

Computing system 400 may receive an indicator of a type of replaceable sound attenuating device 300 of sound attenuating apparatus 100 (910). For example, electronic receiver 200 may transmit the indicator of the type of replaceable sound attenuating device 300 to computing system 400. In examples that do not include an electronic receiver, the type of replaceable sound attenuating device may be transmitted to the test device.

The external and internal microphones may receive a test signal that is detected as an external signal by the external microphone and an internal signal by the internal microphone (920). In some example, the test signal is a broadband signal that includes frequencies that correspond to frequencies used in a reference test, such as the REAT test. For example, the broadband signal may include frequencies of one-third octave bands centered at 125 Hz, 250 Hz, 500 Hz, 1000 Hz, 2000 Hz, 4000 Hz, and 8000 Hz.

Computing system 400 may measure a transfer function between the external signal detected by the external microphone and the internal signal detected by the internal microphone (930). For example, the transfer function may represent a change in amplitude and/or phase between the external signal and the internal signal for a particular frequency.

Computing system 400 may determine an uncompensated attenuation value for each frequency of the test signal based on the transfer function (940). For example, computing system 400 may convert the transfer function into an uncompensated attenuation value or band at a same reference frequency as the reference test, such as the REAT test. The uncompensated attenuation value may by the attenuation value that is uncompensated for differences between the microphone test and the reference test.

Computing system 400 may determine a compensated attenuation value for each frequency of the test signal based on the uncompensated attenuation value and the compensation factors based on the type of replaceable sound attenuating device 300 (950). For example, computing system 400 may look up the compensation factors at the various frequencies, such as in a database or look-up table, and add the compensation factors to the uncompensated attenuation values. Computing system 400 may determine a personal attenuation rating (PAR) for the type of replaceable sound attenuating device 300, or combination of the type of replaceable sound attenuating device 300 and electronic receiver 200, and the user based on the compensated attenuation value for each frequency (960). For example, the compensated attenuation values at each frequency or band may be subtracted from a sound pressure level of an unattenuated noise exposure at the same frequencies or bands, resulting in protected noise levels at each frequency or band. The unattenuated noise exposure bands may be summed logarithmically (in some examples, after being A-weighted or C-weighted) to calculate a broadband unattenuated noise exposure sound level. Similarly, the protected noise levels at each frequency or band may be summed logarithmically to calculate the broadband protected sound level. The PAR may be calculated as an arithmetic difference between the unattenuated exposure sound level and the protected sound level. As another example, computing system 400 may consider a variety of possible unattenuated noise exposures (such as the noise spectra of the NIOSH 100 database of industrial noises), and calculate an average noise reduction across all possible exposures. Other enhancements to the calculation may include accounting for uncertainty in the measured transfer function, the compensation factors, the fit of the device, or other sources of uncertainty.

In some examples, the techniques of FIGS. 6 and 7 may be performed as an initial fit test for replaceable sound attenuating device 300 for a particular user. For example, in the example of FIG. 6, electronic receiver 200 may receive a command as part of an initial diagnostic test to estimate effectiveness of replaceable sound attenuating device 300 within a particular environment and, in response to receiving the command, transmitting the indicator that represents the type of replaceable sound attenuating device 300 to computing system 400. After computing system 400 performs the technique of FIG. 7, computing system 400 may store the PAR for the type of replaceable sound attenuating device 300. Computing system 400 may associate the PAR with the type of replaceable sound attenuating device 300, or combination of the type of replaceable sound attenuating device 300 and electronic receiver 200, for the user.

In some examples, the techniques of FIGS. 6 and 7 may be performed as an in-situ test to estimate effectiveness of replaceable sound attenuating device 300 within a particular environment. For example, in the example of FIG. 6, electronic receiver 200 may receive a command as part of a periodic or on-demand test to estimate effectiveness of replaceable sound attenuating device 300 within a particular environment and, in response to receiving the command, transmitting the indicator that represents the type of replaceable sound attenuating device 300 to computing system 400. For example, the test signal may be a noise received in a working environment. After computing system 400 performs the technique of FIG. 7, computing system 400 may store the PAR for the type of replaceable sound attenuating device 300. Computing system 400 may associate the PAR with the type of replaceable sound attenuating device 300, or combination of the type of replaceable sound attenuating device 300 and electronic receiver 200, and the particular environment in which replaceable sound attenuating device 300 was used.

While FIG. 7 has been described with respect to computing system 400, electronic receiver 200 may be configured to perform any one or more of the steps. For example, electronic receiver may be configured to perform aspects of a fit test and transmit the results of the fit test, including PAR values, to computing system 400.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over a computer-readable medium as one or more instructions or code, and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium.

It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors including processor circuitry. Such processors may include one or more digital signal processors (DSPs), general purpose microprocessors, application specific integrated circuits (ASICs), field programmable gate arrays (FPGAs), or other equivalent integrated or discrete logic circuitry, as well as any combination of such components. Accordingly, the term "processor," as used herein may refer to any of the foregoing structures or any other structure suitable for implementation of the techniques described herein. In addition, in some respects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless communication device or wireless handset, a microprocessor, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

The invention claimed is:

1. An electronic receiver for a replaceable sound attenuating device, comprising:
    a body to physically couple with the replaceable sound attenuating device;
    a transceiver;
    processor circuitry coupled to the transceiver and configured to:
        detect a coupling between the electronic receiver and the replaceable sound attenuating device, the replaceable sound attenuating device comprising a sound attenuating material having a sensor element embedded therein, and
        responsive to the coupling, detect a property of the sensor element that corresponds to a type of the replaceable sound attenuating device; and
    wherein the processor circuitry is further configured to determine the type of the replaceable sound attenuating device as part of an in-situ test to estimate effectiveness of the replaceable sound attenuating device within a particular environment.

2. The electronic receiver of claim 1, wherein the processor circuitry is further configured to determine the type of the replaceable sound attenuating device based on the property of the sensor element.

3. The electronic receiver of claim 1, wherein the processor circuitry is further configured to control the transceiver to transmit, to a computing system over a communication link, an indicator that represents the type of the replaceable sound attenuating device.

4. The electronic receiver of claim 1, further comprising circuitry coupled to the processor circuitry and configured to acquire usage data for the replaceable sound attenuating device, wherein the processor circuitry is further configured to control the transceiver to transmit, to a computing system over a communication link, the usage data for the replaceable sound attenuating device.

5. The electronic receiver of claim 1, further comprising circuitry coupled to the processor circuitry and configured to acquire geo-location data for the replaceable sound attenuating device, wherein the processor circuitry is further configured to control the electronic receiver to generate an audio cue representative of location of the replaceable sound attenuating device based on the geo-location data.

6. The electronic receiver of claim 1, wherein the processor circuitry is further configured to control the electronic receiver to generate an audio cue to indicate effectiveness of the replaceable sound attenuating device within a particular environment based on an noise attenuation rating that is associated with the type of the replaceable sound attenuating device and that is selected from one of capable and incapable to attenuate audio within the particular environment to less than or equal to a threshold safety level.

7. The electronic receiver of claim 6, wherein the noise attenuation rating comprises at least one of a Noise Reduction Rating (NRR), Single Number Rating (SNR), or Sound Level Conversion (SLC).

8. The electronic receiver of claim 6, wherein the noise attenuation rating comprises a personal attenuation rating (PAR) further associated with a user.

9. The electronic receiver of claim 1, further comprising circuitry coupled to the processor circuitry and configured to process audio signals attenuated by the replaceable sound attenuating device and received by the electronic receiver, wherein the processor circuitry is further configured to control the electronic receiver to output audio at a level that is a function of a level of the audio signals attenuated by the replaceable sound attenuating device.

10. The electronic receiver of claim 1, wherein the electronic receiver is configured as a concha-fit device and to interference-fit with the replaceable sound attenuating device.

11. The electronic receiver of claim 1, wherein the electronic receiver is configured as an over-the-ear device and to adhere with the replaceable sound attenuating device.

12. A hearing protection system, comprising:
- a computing system configured to estimate an effectiveness of at least one replaceable sound attenuating device, the at least one replaceable sound attenuating device comprising a sound attenuating material having a sensor element embedded therein; and
- an electronic receiver for the at least one replaceable sound attenuating device, the electronic receiver configured to:
  - mate with the at least one replaceable sound attenuating device,
  - determine a type of the at least one replaceable sound attenuating device based at least on a property of the sensor element as detected by the electronic receiver, and
  - transmit, to the computing system over a communication link, an indicator that represents the type of the at least one replaceable sound attenuating device;
- wherein the computing system is configured to estimate the effectiveness of at least one replaceable sound attenuating device based at least on the indicator.

13. The system of claim 12, wherein the computing system is further configured to aggregate and report usage data associated with each one of the at least one replaceable sound attenuating device and the electronic receiver.

14. A method, comprising:
- detecting, by an electronic receiver for a replaceable sound attenuating device comprising a sound attenuating material having a sensor element embedded therein, a coupling between the electronic receiver and the replaceable sound attenuating device;
- determining, in response to detecting the coupling, a type of the replaceable sound attenuating device based on a property of the sensor element;
- receiving a command as part of an initial diagnostic test to estimate effectiveness of the replaceable sound attenuating device within a particular environment; and
- responsive to the command, transmitting an indicator that represents the type of the replaceable sound attenuating device to a computing system over a communication link.

* * * * *